(12) United States Patent
Thakur

(10) Patent No.: US 6,855,308 B2
(45) Date of Patent: Feb. 15, 2005

(54) PACAP COMPOSITIONS AND METHODS FOR TUMOR IMAGING AND THERAPY

(75) Inventor: Madhukar L. Thakur, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 70 days.

(21) Appl. No.: 10/279,554

(22) Filed: Oct. 21, 2002

(65) Prior Publication Data

US 2003/0129133 A1 Jul. 10, 2003

Related U.S. Application Data

(60) Provisional application No. 60/344,511, filed on Oct. 19, 2001.

(51) Int. Cl.[7] ............................................. A61K 51/00
(52) U.S. Cl. .................... 424/1.69; 424/1.11; 424/1.65; 424/9.1
(58) Field of Search .............................. 424/1.11, 1.65, 424/1.69, 9.1, 9.2, 9.3, 9.4, 9.5, 9.6, 9.7, 9.8; 534/7, 10–16; 530/300, 324

(56) References Cited

U.S. PATENT DOCUMENTS

| | | | |
|---|---|---|---|
| 5,849,261 A | 12/1998 | Dean et al. ................. | 424/1.69 |
| 5,997,844 A | 12/1999 | Dean et al. ................. | 424/1.69 |
| 6,007,792 A | 12/1999 | Dean et al. ................. | 424/1.69 |
| 6,074,627 A | 6/2000 | Dean et al. ................. | 424/1.69 |
| 6,086,849 A | 7/2000 | Dean et al. ................. | 424/1.69 |
| 6,107,459 A | 8/2000 | Dean ........................ | 530/326 |
| 6,113,878 A | 9/2000 | Dean et al. ................. | 242/1.69 |
| 6,165,755 A | 12/2000 | Sherwood et al. ......... | 435/69.4 |
| 6,395,255 B1 | 5/2002 | Thakur ...................... | 424/1.69 |

OTHER PUBLICATIONS

Basille M et al., *Brain Res.* 82: 81–89, 1994.
Behr TM et al., *Eur. J. Nucl. Med.* 25: 201–212, 1998.
Bernard BF et al., *J. Nucl. Med.* 38: 1929–1933, 1997.
Bolin DA et al., *Drug Design and Discovery* 13: 107–114, 1996.
Fischman AJ et al., *J. Nucl. Med.* 34: 2253–2263, 1993.
Gottschall PE et al., *Endocrinology* 127: 272–277, 1990.
Harmar T et al., *TiPs* 15: 97–99, 1994.
Hokfelt T, *Neuron* 7: 867–879, 1991.
Kobayashi H et al., *Cancer Res.* 56: 3788–3795, 1996.
Krenning EP et al., *Eur. J. Nucl. Med.* 20: 716–731, 1993.
Le Meuth V et al., *Amer. J. Physiol.* 260: G265–74, 1991.
Lelievre V et al., *Neuropeptides* 30: 313–322, 1996.
McCready VR et al, *Lancet* 343: 617, 1994.
Miyata A et al., *Biochem. Biophys. Res. Commun.* 164: 567–574, 1989.
Olianas MC et al., *J. Neurochem.* 67: 1293–1300, 1996.
Pallela VR et al., *Jour. Nucl. Med.*, vol. 40, No. 2, pp. 352–360, Feb. 1999.
Parkman HP et al., *Regulatory Peptides* 71: 185–190, 1998.
Reubi JC et al., *Cancer Res.* 60: 3105–3112, 2000.
Reubi JC et al., *Eur. J. Nucl. Med.* 24: 1058, 1997.
Reubi JC et al., *J. Nucl. Med.* 36: 1846–1853, 1995.
Thakur ML, et al., *J. Nucl. Med.* 41: 107–110, 2000.
Van Eijck CH et al., *Lancet* 343: 640–643, 1994.
Vertrongen P et al., *Neuropeptides* 30: 491–496, 1996.
Zia F et al., *Cancer Res.* 55: 4886–4891, 1995.
Zia H et al., *Cancer Res.* 56: 3486–3489, 1996.
Vertongen P et al., *Neuropeptides* 30 (5), 491–496, 1996.
Lelievre V et al., *Neuropeptides* 30 (4), 313–322, 1996.
Rattan, et al., "Excitatory And Inhibitory Actions Of Pituitary Adenylate Cyclase–Activating Peptide (PACAP) In The Internal Anal Sphincter Smooth Muscle: Sites Of Actions", *J. Pharmcol. Exp. Thera.*, 238:722–728, (1997).

*Primary Examiner*—Dameron L. Jones
(74) *Attorney, Agent, or Firm*—Drinker Biddle & Reath LLP

(57) ABSTRACT

Tumors expressing VPAC receptors can be imaged or treated with compounds comprising PACAP, or a biologically active PACAP fragment or analog.

45 Claims, 5 Drawing Sheets

His-Ser-Asp-Gly-Ile-Phe-Thr-Asp-Ser-Tyr-Ser-Arg-Tyr-Arg-Lys-Gln-Met-Ala-
Val-Lys-Lys-Tyr-Leu-Ala-Ala-Val-Leu-Aba*-Gly-(D)Ala-Gly-Gly- (Resin)

↓ (i)

His-Ser-Asp-Gly-Ile-Phe-Thr-Asp-Ser-Tyr-Ser-Arg-Tyr-Arg-Lys-Gln-Met-Ala-
Val-Lys-Lys-Tyr-Leu-Ala-Ala-Val-Leu-Aba*-Gly-(D)Ala-Gly-Gly

↓ (ii)

His-Ser-Asp-Gly-Ile-Phe-Thr-Asp-Ser-Tyr-Ser-Arg-Tyr-Arg-Lys-
Gln-Met-Ala-Val-Lys-Lys-Tyr-Leu-Ala-Ala-Val-Leu-Aba*-CO-NH

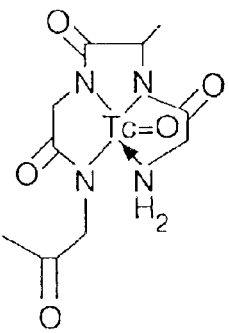

*4-aminobutyric acid (i) TFA / Thioanisole / Ethanedithiol / Phenol (90 : 5 : 3 : 2)
(ii) Na$^{99m}$TcO$_4$ /SnCl$_4$ /Na$_3$PO$_4$ (pH 12)

FIG. 2

SEQUENCE LISTING

<160> NUMBER OF SEQ ID NOS: 5

<210> SEQ ID NO 1
<211> LENGTH: 38
<212> TYPE: PRT
<213> ORGANISM: Homo sapiens

<400> SEQUENCE: 1

```
His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Gly Lys Arg Tyr Lys
            20                  25                  30

Gln Arg Val Lys Asn Lys
```

```
<210> SEQ ID NO 2
<211> LENGTH: 27
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu
            20                  25

<210> SEQ ID NO 3
<211> LENGTH: 176
<212> TYPE: PRT
<213> ORGANISM: Homo sapiens

<400> SEQUENCE: 3

Met Thr Met Cys Ser Gly Ala Arg Leu Ala Leu Leu Val Tyr Gly Ile
 1               5                  10                  15

Ile Met His Ser Ser Val Tyr Ser Ser Pro Ala Ala Gly Leu Arg
            20                  25                  30

Phe Pro Gly Ile Arg Pro Glu Glu Ala Tyr Gly Glu Asp Gly Asn
        35                  40                  45

Pro Leu Pro Asp Phe Gly Gly Ser Glu Pro Gly Ala Gly Ser Pro
    50                  55                  60

Ala Ser Ala Pro Arg Ala Ala Ala Trp Tyr Arg Pro Ala Gly Arg
65                  70                  75                  80

Arg Asp Val Ala His Gly Ile Leu Asn Glu Ala Tyr Arg Lys Val Leu
                85                  90                  95

Asp Gln Leu Ser Ala Gly Lys His Leu Gln Ser Leu Val Ala Arg Gly
                100                 105                 110

Val Gly Gly Ser Leu Gly Gly Gly Ala Gly Asp Asp Ala Glu Pro Leu
            115                 120                 125

Ser Lys Arg His Ser Asp Gly Ile Phe Thr Asp Ser Tyr Ser Arg Tyr
        130                 135                 140

Arg Lys Gln Met Ala Val Lys Lys Tyr Leu Ala Ala Val Leu Gly Lys
145                 150                 155                 160

Arg Tyr Lys Gln Arg Val Lys Asn Lys Gly Arg Arg Ile Ala Tyr Leu
                165                 170                 175

<210> SEQ ID NO 4
<211> LENGTH: 4
<212> TYPE: PRT
<213> ORGANISM: Artificial Sequence
<220> FEATURE:
<223> OTHER INFORMATION: N4 chelating agent
<220> FEATURE:
<221> NAME/KEY: VARIANT
<222> LOCATION: 2
<223> OTHER INFORMATION: D-form

<400> SEQUENCE: 4

Gly Ala Gly Gly
 1

<210> SEQ ID NO 5
<211> LENGTH: 32
<212> TYPE: PRT
<213> ORGANISM: Artificial Sequence
```

-continued

```
<220> FEATURE:
<223> OTHER INFORMATION: PACAP analog TP 3475
<220> FEATURE:
<221> NAME/KEY: VARIANT
<222> LOCATION: 28
<223> OTHER INFORMATION: Xaa = 4-aminobutyric acid
<220> FEATURE:
<221> NAME/KEY: VARIANT
<222> LOCATION: 30
<223> OTHER INFORMATION: D-form

<400> SEQUENCE: 5

His Ser Asp Gly Ile Phe Thr Asp Ser Tyr Ser Arg Tyr Arg Lys Gln
 1               5                  10                  15

Met Ala Val Lys Lys Tyr Leu Ala Ala Val Leu Xaa Gly Ala Gly Gly
             20                  25                  30
```

PACAP COMPOSITIONS AND METHODS FOR TUMOR IMAGING AND THERAPY

CROSS REFERENCE TO RELATED APPLICATION

This application claims the benefit of U.S. provisional patent application Ser. No. 60/344,511, filed on Oct. 19, 2001, the disclosure of which is herein incorporated by reference in its entirety.

FIELD OF THE INVENTION

The present invention generally relates to the field of nuclear medicine and to molecular tumor imaging or therapeutic agents and, more particularly, to radiolabeled agents for imaging or treating tumors expressing VPAC receptors.

BACKGROUND OF THE INVENTION

Cancer is a formidable cell proliferative disease that takes millions of lives each year. With breast cancer alone, more than 50,000 women in the United States are afflicted annually. Breast tumors are traditionally detected by ultrasound, MRI, or mammography followed by histology, and are treated by surgical resection followed by chemo- and/or radiation therapy. Mortality from breast (and other) cancers can be reduced through early diagnosis and treatment of tumors (Kelsey J L, *Epidemiol. Rev.* 1: 74–109, 1989). An effective method for the early detection of tumors is scintigriphic imaging with tumor-specific radioactive imaging agents.

A number of radioactive tumor imaging agents have been used for detecting breast tumors, with varying degrees of success. For example, receptor specific biomolecules, such as neuropeptides, bind to receptors in nanomolar concentrations and have been the focus of a considerable interest both in the therapeutic and diagnostic fields (Fischman A J et al., *J. Nucl. Med.* 34: 2253–2263, 1993; Hokfelt T *Neuron* 7: 867–879, 1991).

However, the only commercially available neuropeptide imaging agent, $^{111}$In-[DTPA-D-Phe$^1$] Octreotide, has not been highly successful in detecting breast tumors (van Eijck C H J et al. *Lancet* 343: 640–643, 1994; McCready V R et al. *Lancet* 343: 617, 1994). van Eijck et al., 1994, supra report that in 52 primary breast cancers, only 75% positive scintigraphy was achieved with this agent. Furthermore, van Eijck et al. showed that imaging of axillae with $^{111}$In-[DTPA-D-Phe$^1$] Octreotide detected non-palpable, cancer-containing lymph nodes in only 4 of 13 patients with histologically-proven metastases. The low efficacy of $^{111}$In-[DTPA-D-Phe$^1$] Octreotide for imaging breast tumors is attributed to the low density of oncogene receptors expressed on breast tumor cells which are specific for the agent. The usefulness of $^{111}$In-[DTPA-D-Phe$^1$] Octreotide for imaging breast tumors is therefore limited.

$^{123}$I-Tyr3-octreotide has also been used for radiodiagnostic imaging, but this agent has not been evaluated for imaging of breast tumors (Krenning E P et al., *Eur. J. Nucl. Med.* 20: 716–731, 1993). However, based on the poor ability of $^{111}$In-[DTPA-D-Phe$^1$] Octreotide to image breast tumors, $^{123}$I-Tyr3-octreotide is not expected to be a useful breast tumor imaging agent.

In any case, radio-iodinated agents are generally not desirable for use as imaging or therapeutic agents, because approved radio-iodinated radiopharmaceuticals normally cannot be prepared at the clinical site. Radio-iodinated agents have specific limitations as well; for example, $^{125}$I-labeled agents are typically not used for imaging applications due to the relatively long half-life (about 59 days) and low emission energy of the radionuclide. $^{123}$I-labeled agents are not preferred, because $^{123}$I is a cyclotron-generated radionuclide which is expensive to produce and the radionuclide has too short a half-life (13.3 hours) to be commercially useful. $^{131}$I-labeled agents have too high an emission energy for quality scintigriphic imaging.

Technetium-99m ($^{99m}$Tc) is widely used in diagnostic imaging agents because it emits gamma radiation at 140 KeV, has a physical half-life of 6 hours, and is easily produced on-site using a molybdenum-99/$^{99m}$Tc generator. The shorter half-life of $^{99m}$Tc minimizes the radiation dose to normal organs, and its emission energy allows efficient detection by gamma cameras. $^{99m}$Tc is therefore the radionuclide of choice in nearly 90% of clinical nuclear medicine applications.

Imaging agents are typically labeled with $^{99m}$Tc through a metal chelating moiety. The $^{99m}$Tc metal chelating moiety is generally also able to complex therapeutic radionuclides such as $^{186}$Re and $^{188}$Re. Thus, a single agent comprising a metal chelator can advantageously be used as a diagnostic or therapeutic agent, depending on which radionuclide is employed.

U.S. Pat. No. 6,395,255 to M. Thakur discloses a method for labeling a vasoactive intestinal peptide (VIP)-based agent using a $^{99m}$Tc chelator. The chelator and labeling chemistry disclosed in U.S. Pat. No. 6,395,255 is suitable for labeling VIP agents with either $^{99m}$Tc or rhenium radionuclides. However, the VIP agents disclosed in U.S. Pat. No. 6,395,255 bind only to tumor cells expressing VIP receptors. As certain tumors express other types of receptors at high density, an imaging or therapeutic agent which can bind to a wider range of receptors expressed by these tumor cells would be advantageous.

Pituitary adenylate cyclase activating peptide (PACAP) is a 38-amino acid peptide originally isolated from bovine hypothalamus (Miyata A et al, *Biochem. Biophys. Res. Commun.* 164: 567–574, 1989). This peptide stimulates the accumulation of intracellular and extracellular cAMP in monolayer cultures of rat anterior pituitary cells (Gottschall P E et al., *Endocrinology* 127: 272–277, 1990). Gottschall et al., 1990, supra isolated a 27-amino acid PACAP (PACAP$_{27}$) from bovine hypothalamus, and concluded that PACAP$_{38}$ and PACAP$_{27}$ were equally active, and were derived from a single 176-amino acid precursor.

PACAP$_{27}$ is ten times more potent than the 28-amino acid vasoactive intestinal peptide VIP$_{28}$ in stimulating adenylate cyclase in pituitary cells (Gottschall et al., 1990, supra). $^{125}$I-PACAP$_{27}$ is also capable of displacing VIP$_{28}$ bound to normal lung membrane. The IC$_{50}$ value for VIP$_{28}$ is approximately 15 nM, and the IC$_{50}$ value for PACAP$_{27}$ is approximately 1.5 nM.

PACAP$_{27}$ binds with high affinity to PACAP, VIP-R1 and VIP-R2 receptors, whereas VIP$_{28}$ binds with high affinity only to VIP-R1 and VIP-R2 receptors (Zia F et al., *Cancer. Res.* 55: 4886–4891, 1995). The PACAP, VIP-R1 and VIP-R2 receptors, referred to collectively as VPAC receptors (Reubi J C, *J. Nucl. Med.* 36: 1846–1853, 1995; Reubi J C et al., *Cancer Res.* 60: 1305–1312, 2000), are expressed in high density on breast tumor (Zia H et al., *Cancer Res.* 56: 3486–3489, 1996) and other tumor cells (Harmar T et al., *TiPs* 15: 97–98, 10 1994; Reubi J C et al., *Eur. J. Nucl. Med.* 24: 1058, 1997; Le Meuth V et al., *Amer. J. Physiol.* 260: G265–74, 1991; Basille M et al. *Brain Res.* 82: 1–2, 1994; Vertrongen P et al., *Neuropeptides* 30: 491–496, 1996; Olianas M C et al., *J. Neurochem.* 67: 1292–1300, 1996; Lelievre V et al., *Neuropeptides* 30: 313–322, 1996; and Parkman H P et al., *Regulatory Peptides* 71: 185–190, 1998). For example, tumors (other than breast tumors) which express VPAC receptors include ovarian, endometrial, prostate, bladder, lung, esophageal, colonic, pancreatic, neuroendocrine and brain tumors.

However, there has been little success in producing a targeted radiopharmaceutical using PACAP. See, for example, Reubi J C et al., *Eur. J. Nucl. Med.* 24: 1058, 1997, who showed that the biological activity of $PACAP_{27}$ linked to DTPA at its N-terminus was reduced from 100 to <0.01.

What is needed, therefore, is a radioactive tumor imaging or therapeutic agent based on a receptor-specific biomolecule such as PACAP, which binds with high affinity to one or more types of receptors present on certain tumor cells. The imaging or therapeutic agent should ideally be labeled with a diagnostic or therapeutic radionuclide through a metal chelator.

SUMMARY OF THE INVENTION

The present invention is directed to the use of radiolabeled PACAP and biologically active PACAP fragments and analogs for imaging or therapy of breast and other tumors which express PACAP, VIP-R1 and VIP-R2 receptors. PACAP, VIP-R1 and VIP-R2 receptors are hereinafter collectively referred to as "VPAC receptors."

Thus, the present invention provides a method of detecting tumors expressing VPAC receptors, comprising administering an effective amount of an imaging compound of formulae A or B to a subject who has, or is suspected of having, such a tumor. After administration of the imaging compound, a scintigriphic image is generated of at least part of the subject's body. Formulae A and B are $M(I)\text{-}X_1\text{-}P\text{-}X_2$ (A)

$X_1\text{-}P\text{-}X_2\text{-}M(I)$. (B)

For both formula A and B:
M is a chelating agent
(I) is an imaging radionuclide conjugated to M;
$X_1$ is from zero to twenty natural or synthetic amino acids;
P is PACAP, or an analog or fragment thereof; and
$X_2$ is from zero to twenty natural or synthetic amino acids.

The invention also provides a method of inhibiting or reversing growth of a tumor expressing VCAP receptors in a subject who has a such a tumor, comprising administering an effective amount of an therapeutic compound of formulae C or D to a subject who has, or is suspected of having, such a tumor. Formulae C and D are $M(T)\text{-}X_1\text{-}P\text{-}X_2$ (C)

$X_1\text{-}P\text{-}X_2\text{-}M(T)$. (D)

For both formula C and D:
M is a chelating agent
(T) is an therapeutic radionuclide conjugated to M;
$X_1$ is from zero to twenty natural or synthetic amino acids;
P is PACAP, or an analog or fragment thereof; and
$X_2$ is from zero to twenty natural or synthetic amino acids.

BRIEF DESCRIPTION OF THE FIGURES

FIG. 2 is a schematic of the preparation and labeling of $^{99m}$Tc-TP 3475, an imaging agent according to the invention.

ABBREVIATIONS

Figure 1A:
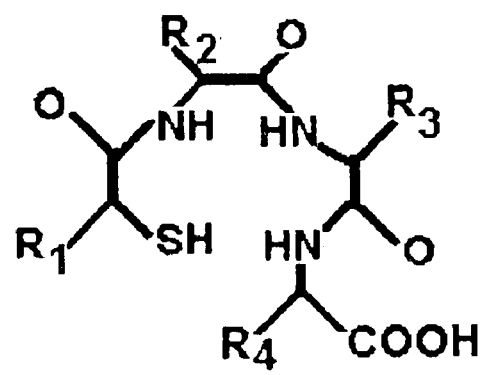
FIGS. 1A and 1B are, respectively, structural representations of MAG3 and Gly-(D)Ala-Gly-Gly. In MAG3, R1=R2=R3=R4=H. In the tetrapeptide, R1=R2=R4=H and R3=CH3.

Aba—4-aminobutyric acid
ADP—adenosine 5'-diphosphate
cAMP—cyclic adenosine monophosphate
CPTA—[4-(1,4,8,11-tetraazacyclotetradec-1-yl)methyl]benzoic acid
HT-29—a human colorectal tumor cell line
$IC_{50}$—50% inhibitory concentration
% ID/g—percent injected dose per gram tissue
Kd—dissociation constant
LS174T—a human colorectal tumor cell line
mCi—milliCurie
MAG3—[N-[N[N-(benzylthio)acetyl]glycyl]glycyl]glycine
MD MB 231—an estrogen-independent human breast tumor cell line
PACAP—pituitary adenylate cyclase activating peptide
RIA—radioimmuno assay
Rt—retention time
T47D—an estrogen-dependent human breast tumor cell line
TFA—trifluoroacetic acid
VIP—vasoactive intestinal peptide

Amino Acid Abbreviations

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| A | Alanine | Ala |
|---|---------|-----|
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

Definitions

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their biological activity. Additionally, a disulfide linkage may be present or absent in the peptides of the invention.

Amino acids have the following general structure:

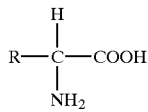

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

A compound which has "PACAP biological activity" means a compound which stimulates at least about ten times the adenylyl cyclase activity, or increases nuclear oncogene expression by at least about ten-fold, as the equivalent amount of $VIP_{28}$ in estrogen-independent (MDA MB 231) or estrogen-dependent (T47D) human breast cancer cells by the assays described in Example 3 below.

"Isolated" means altered or removed from the natural state through the actions of a human being. For example, a nucleic acid sequence or a peptide naturally present in a living animal is not "isolated," but the same nucleic acid or peptide partially or completely separated from the coexisting materials of its natural state is "isolated." An isolated nucleic acid sequence or protein may exist in substantially purified form, or may exist in a non-native environment such as, for example, a host cell.

As used herein, "protecting group" with respect to a terminal amino group of a peptide means any of the various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3–88 (Academic Press, New York, 1981) for suitable protecting groups.

As used herein, "protecting group" with respect to a terminal carboxy group of a peptide means any of various carboxyl-terminal protecting groups traditionally employed in peptide synthesis. Such protecting groups include, for example, tert-butyl, benzyl or other acceptable groups linked to the terminal carboxyl group through an ester or ether bond.

"Analog" includes any naturally occurring or purposefully generated PACAP which is characterized by single or multiple amino acid substitutions, deletions, additions, or replacements, but which retains PACAP biological activity. Such analogs include (a) analogs in which one or more amino acid residues of PACAP are substituted with conservative or non-conservative amino acids; (b) analogs in which one or more amino acids are added; (c) analogs in which one or more of the amino acids include a substituent group not normally present on the amino acid; (d) analogs in which PACAP or a portion thereof is fused to another peptide; (e) analogs in which one or more nonstandard amino acid residues (i.e., those other than the 20 standard L-amino acids found in naturally occurring proteins) are incorporated or substituted into the PACAP sequence; and (f) analogs in which one or more nonamino acid linking groups are incorporated into or replace a portion of PACAP.

"Peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which may comprise a protein or peptide. The amino acids comprising the peptides or proteins described herein and in the appended claims are understood to be either D or L amino acids with L amino acids being preferred. The amino acid comprising the peptides or proteins described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Also, a given peptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W.H. Freeman and Company, New York, 1993 and Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Posttranslational Modifications and Aging", Ann N.Y. Acad Sci (1992) 663:48–62, the entire disclosures of which are herein incorporated by reference.

As used herein, a peptide or a portion of a peptide which has a "substantially similar amino acid sequence" to a reference protein means the peptide, or a portion thereof, has an amino acid sequence identity or similarity to the reference protein of greater than about 80%. Preferably, the sequence identity is greater than about 85%, more preferably greater than about 90%, particularly preferably greater than about 95%, and most preferably greater than about 98%. As used herein, "sequence identity" with respect to a reference peptide can be computed by using the BLASTP and TBLASTN programs which employ the BLAST (basic local alignment search tool) 2.0.14 algorithm; BLASTP and TBLASTN settings to be used in such computations are indicated in Table 1 below. Amino acid sequence identity is reported under "Identities" by the BLASTP and TBLASTN programs. Techniques for computing amino acid sequence identity are well known to those skilled in the art, and the use of the BLAST algorithm is described in Altschul et al. (1990), *J. Mol. Biol.* 215: 403–10 and Altschul et al. (1997), *Nucleic Acids Res.* 25:3389–3402, the entire disclosures of which are herein incorporated by reference. BLASTP and TBLASTN programs utilizing the BLAST 2.0.14 algorithm.

TABLE 1

Settings to be used for the computation of amino acid sequence identity with BLASTP and TBLASTN programs utilizing the BLAST 2.0.14 algorithm.

| | |
|---|---|
| Expect Value | 10 |
| Filter | Low complexity filtering using SEG program* |
| Substitution Matrix | BLOSUM62 |
| Gap existence cost | 11 |
| Per residue gap cost | 1 |
| Lambda ratio | 0.85 |
| Word size | 3 |

*The SEG program is described by Wootton and Federhen, Comput. Chem. 17: 149–163, 1993.

DETAILED DESCRIPTION OF THE INVENTION

Tumor-specific diagnostic imaging and therapeutic compounds comprising PACAP, or biologically active analog or fragment of PACAP, are advantageously used to image or treat tumors which express VPAC receptors. Both a 38- and a 27-amino acid form of PACAP have been isolated, which are known as $PACAP_{38}$ and $PACAP_{27}$, respectively. The primary amino acid sequence of $PACAP_{38}$ is given in SEQ ID NO: 1. The primary amino acid sequence of $PACAP_{27}$ is given in SEQ ID NO: 2. $PACAP_{38}$ and $PACAP_{27}$ are derived from the same 176 amino acid PACAP precursor protein, the sequence of which is given in SEQ ID NO: 3. As used herein, the term "PACAP" includes the $PACAP_{38}$ (SEQ ID NO: 1), $PACAP_{27}$ (SEQ ID NO: 2) and 176 amino acid PACAP precursor protein (SEQ ID NO: 3).

PACAP can be isolated from bovine hypothalamus according to known techniques; see, for example, Miyata A et al, *Biochem. Biophys. Res. Commun.* 164: 567–574, 1989 and Gottschall P E et al., *Endocrinology* 127: 272–277, 1990, the entire disclosures of which are herein incorporated by reference. PACAP can also be produced synthetically by any known means, including synthesis by biological systems and by chemical methods.

Biological synthesis of peptides is well known in the art, and includes the transcription and translation of a naturally-occurring or synthetic gene encoding PACAP nucleic acid sequences. These nucleic acids can be subcloned into an appropriate plasmid expression vector for propagation and expression in an appropriate host cell. Techniques for constructing nucleic acid sequences and plasmid expression vectors, transfecting host cells, and expressing a nucleic acid sequence of interest are widely practiced in the art, and practitioners of ordinary skill are familiar with the standard resource materials which describe specific conditions and procedures. For example, general methods for the cloning and expression of recombinant molecules are described in Sambrook et al., *Molecular Cloning*, Cold Spring Harbor Laboratories, 1982; and in Ausubel, *Current Protocols in Molecular Biology*, Wiley and Sons, 1987, the entire disclosures of which are incorporated herein by reference.

Chemical peptide synthesis techniques (including manual and automated techniques) which are suitable for directly synthesizing PACAP are also well-known to those of ordinary skill in the art. For example, PACAP can be synthesized de novo using conventional solid phase synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldimidazole; various active esters, e.g., esters of N-hydroxyphthalimide or N-hydroxy-succinimide; and the various cleavage reagents, e.g., trifluoroactetic acid (TFA), HCl in dioxane, boron tris-(trifluoracetate) and cyanogen bromide; and reaction in solution with isolation and purification of intermediates are well-known to those of ordinary skill in the art. A preferred chemical peptide synthesis method follows conventional Merrifield solid phase procedures well known to those skilled in the art. Additional information about solid phase synthesis procedures can be had by reference to Steward and Young, *Solid Phase Peptide Synthesis*, W.H. Freeman & Co., San Francisco, 1969; the review chapter by Merrifield in *Advances in Enzymology* 32:221–296, (Nold F F, ed.), Interscience Publishers, New York, 1969; and Erickson and Merrifield (1990), *The Proteins* 2:61–64, the entire disclosures of which are herein incorporated by reference.

The present imaging and therapeutic agents also comprise biologically active fragments of PACAP. Biologically active PACAP fragments according to the invention can be obtained, for example, by chemical or enzymatic fragmentation of larger natural or synthetic PACAP, or by biological or chemical syntheses as described above.

The present imaging and therapeutic agents also comprise biologically active analogs of PACAP. The techniques for obtaining such analogs are known to persons having ordinary skill in the art and include, for example, standard recombinant nucleic acid techniques, solid phase peptide synthesis techniques and chemical synthetic techniques as described above. Linking groups may also be used to join or replace portions of PACAP and other peptides. Linking groups include, for example, cyclic compounds capable of connecting an amino-terminal portion and a carboxyl terminal portion of PACAP. Techniques for generating analogs are also described in U.S. Pat. No. 6,030,942 the entire disclosure of which is herein incorporated by reference (analogs are designated "peptoids" in the U.S. Pat. No. 6,030,942).

PACAP analogs also include fusion peptides in which a portion of the fusion peptide has a substantially similar amino acid sequence to PACAP. Such fusion peptides can be generated by techniques well-known in the art, for example by subcloning nucleic acid sequences encoding an PACAP and a heterologous peptide sequence into the same expression vector, such that the PACAP and the heterologous sequence are expressed together in the same protein.

The imaging and therapeutic compounds of the invention are formed by linking PACAP, or biologically active fragments or analogs thereof, to a metal chelating agent. As used herein, "linked" means covalently bonded. The chelating agent is then conjugated with an imaging or therapeutic radionuclide. The chelating agent can be linked with the PACAP, or biologically active PACAP fragment or analog, at any point on the peptide structure which does not interfere with the PACAP biological activity of the resulting compound. Preferably, the chelating agent is linked to the PACAP, or biologically active PACAP fragment or analog, at the N- or C-terminus of the peptide, and more preferably to the C-terminus of the peptide.

The imaging or therapeutic compounds of the invention preferably comprise a "spacer" of one or more natural or synthetic amino acids linked to either the N- or C-terminus of PACAP or biologically active PACAP fragments or analogs. The chelating agent can then be linked to this spacer. The spacer minimizes steric hindrance from the radionuclide or chelating agent, and helps preserve PACAP biological activity in the imaging or therapeutic compound.

Thus, in formulae A and B for the imaging compounds of the invention, and formulae C and D for the therapeutic compounds of the invention given above, the optional spacer can be represented as either $Z_1$ or $Z_2$, which link $X_1$ or $X_2$ to M, respectively. The formulae with the optional spacer are given below:

$M(I)$-$Z_1$-$X_1$-P-$X_2$ (A)

$X_1$-P-$X_2$-$Z_2$-$M(I)$ (B)

$M(T)$-$Z_1$-$X_1$-P-$X_2$ (C)

$X_1$-P-$X_2$-$Z_2$-$M(T)$ (D)

The remaining variables in these formulae are as described above in the Summary of the Invention.

The spacer $Z_1$ or $Z_2$ can comprise, for example, 1 to 20 amino acids, preferably 1 to 4 amino acids, and more preferably 1 amino acid. A particularly preferred spacer comprises 4-amino butyric acid, also known as "Aba."

Chelating agents can comprise the residue of one or more of a wide variety of chelating compounds that can complex a metal ion or a polyatomic ion (e.g., TcO). As used herein, a "chelating agent" is a compound that can be linked to a PACAP, or a biologically active PACAP fragment or analog, and which contains donor atoms that can conjugate with a metal atom. The chelating agent conjugates to a metal atom by coordinate bonding, and forms a cyclic structure called a "chelation complex" or "chelate."

Chelating agents suitable for use in the present invention include NxSy chelating compounds. As used herein, the term "NxSy chelating compound" means chelating agents that are capable of coordinately binding a metal radionuclide and capable of being linked to PACAP, or a biologically active analog or fragment of PACAP, which chelating agents have cores of the following configurations: N2S2 (e.g., as described in U.S. Pat. Nos. 4,897,225; 5,164,176; or 5,120, 526); N3 (e.g., as described in U.S. Pat. No. 4,965,392); N2S3 (e.g., as described in U.S. Pat. No. 4,988,496), N2S4 (e.g., as described in U.S. Pat. No. 4,988,496), N3S3 (e.g., as described in U.S. Pat. No. 5,075,099); N4 (e.g., as described in U.S. Pat. No. 4,963,688 and U.S. Pat. No. 5,227,474) or NS3. Preferred NxSy chelating compounds comprise N2S2, N3S or N4 cores. Exemplary NxSy chelating compounds are also described in Fritzberg et al., *P.N.A.S. USA* 85:4024–29, 1988 and Weber et al., *Bioconj. Chem.* 1:431–37, 1990. The disclosures of the journal articles and U.S. patents identified in this paragraph are herein incorporated by reference in their entirety.

Figure 1B:
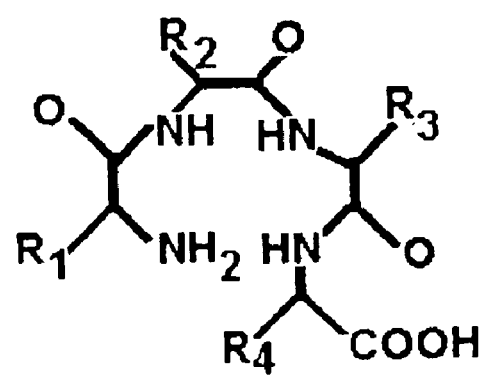

Particularly preferred N4 chelating agents are [N-[N[N-(benzylthio)acetyl]glycyl]glycyl]glycine, also known as mercapto acetyl triglycine or MAG3, and the tetrapeptide Gly-(D)Ala-Gly-Gly (SEQ ID NO: 4) which is described in Vanbilloen H P et al., *Nucl. Med. Biol.* 22: 325–338, 1995, the entire disclosure of which is herein incorporated by reference. Gly-(D)Ala-Gly-Gly is a derivative of MAG3 in which the mercapto group is replaced with a more stable and easy-to-incorporate amino group. This structures of both N4 chelating agents are shown in FIG. 1.

This sequence of Gly-(D)Ala-Gly-Gly can be incorporated either at the N- or C-terminus, preferably the C-terminus, of PACAP or a biologically active PACAP fragment or analog during the synthesis of the peptide. This process is preferred, because it eliminates the need for separately linking a chelating agent to the peptide, which might include blocking and deblocking functional groups on the peptide, purifying the reaction mixture by HPLC procedure and identifying the desired product by mass spectrophotometric analysis. As discussed above, Aba can be used as a spacer between Gly-(D)Ala-Gly-Gly and PACAP or a biologically active PACAP fragment or analog. Aba can be linked to PACAP, or a biologically active PACAP fragment or analog, during peptide synthesis without additional steps. The production of peptide compounds with a MAG3 or Gly-(D)Ala-Gly-Gly chelating agent, linking these chelating agents to the peptide with Aba, and conjugating the linked chelating agents with an imaging or therapeutic radionuclide are described in U.S. Pat. No. 6,395,255, the entire disclosure of which is herein incorporated by reference.

Methods for linking NxSy chelating compounds to proteins are known in the art; for example as disclosed in U.S. Pat. No. 5,175,257 and U.S. Pat. No. 6,171,577, the entire disclosures of which are herein incorporated by reference. For example, an NxSy chelating compound can be linked to PACAP, or biologically active fragments or analogs of PACAP, with a chemically reactive "linking group," which is reactive under conditions that do not denature or otherwise adversely affect the protein. The linking group can be separate from, or integral to, the chelating agent. Chelating agents which have integral linking groups are known as "bifunctional chelating agents." The linking group is sufficiently reactive with a functional group on the protein so that the reaction can be conducted in a substantially aqueous solution, and does not have to be forced; e.g., by heating to high temperatures which may denature the protein.

Examples of suitable linking groups include active esters, isothiocyanates, amines, hydrazines, maleimides or other Michael-type acceptors, thiols, and activated halides. Among the preferred active esters are N-hydroxysuccinimidyl ester, sulfosuccinimidyl ester, thiophenyl ester, 2,3,5,6-tetrafluorophenyl ester, and 2,3,5, 6-tetrafluorothiophenyl ester. The latter three active esters may comprise a group that enhances water solubility, at the para (i.e., 4) or the ortho position on the phenyl ring. Examples of such groups are $CO_2H$, $SO_3^-$, $PO_3^{2-}$, $OPO_3^{2-}$, $OSO_3^-$, and $N^+R_3$ wherein each R represents H or an alkyl group.

Other suitable chelating agents for use in the present invention include linear, cyclic and branched polyamino-polycarboxylic acids and their phosphorous oxyacid equivalents, for example ethylenediamine-N,N,N',N'-tetraacetic acid (EDTA); N,N,N',N'',N''-diethylene-triaminepentaacetic acid (DTPA); 1,4,7,10-tetraazocyclododecane-N,N'N'',N'''-tetraacetic acid (DOTA); 1,4,7,10-tetraazo-cyclododecane-N,N'N''-triacetic acid (DO3A); 1-oxa-4,7,10-triazacyclododecane-N,N'N''-triacetic acid (OTTA); trans(1,2)-cyclohexanodiethylene-triamine-pentaacetic acid (CDTPA); 1-oxa-4,7,10-triazacyclododecantriaacetic acid (DOXA); 1,4,7-triazacyclononanetriacetic acid (NOTA); and 1,4,8,11-tetraazacyclotetradecanetetraacetic acid (TETA).

Such chelating agents can be linked to PACAP by any suitable method, as is known in the art. For example, the chelating agent can be linked to PACAP via one of the metal coordinating groups, which can form an ester, amide thioester or thioamide bond with an amine, thiol or hydroxy group on PACAP. Alternatively, the chelating agent can be linked to PACAP via a functional group attached directly to the chelating agent; e.g., a CH2-phenyl-NCS group attached to a ring carbon of DOTA as described in Meares et al., *JACS* 110: 6266–6267, the entire disclosure of which is herein incorporated by reference. The chelating agent can also be linked to PACAP indirectly with a homo- or hetero-bifunctional linker; e.g., a bis amine, bis epoxide, diol, diacid, or a difunctionalized PEG. As above, chelating agents which have integral linking groups are known as "bifunctional chelating agents." Preferably, the polyamino-polycarboxylic acid chelating agent is linked to the PACAP, or biologically active PACAP fragment or analog, at C-terminus of the peptide.

Suitable methods for metallating chelating agents linked to PACAP, or biologically active fragments or analogs of PACAP with an imaging or therapeutic radionuclide are within the skill in the art; e.g., as described in U.S. Pat. No. 5,175,257 and U.S. Pat. No. 6,171,577, the entire disclosures of which are herein incorporated by reference. For example, imaging or therapeutic radionuclides can be incorporated into a compound of the invention by direct incorporation, template synthesis and/or transmetallation. Direct incorporation is preferred.

For direct incorporation, the imaging or therapeutic radionuclide must be easily complexed by the chelating agent; for example, by merely exposing or mixing an aqueous solution of chelating agent-containing compound with a metal salt in an aqueous solution. The metal salt can be any salt, but is preferably a water soluble salt of the metal such as a halogen salt. More preferably, such salts are selected so as not to interfere with the binding of the metal ion with the chelating agent. The chelating agent-containing compound can be mixed with buffer salts such as citrate, acetate, phosphate and/or borate to produce the optimum pH for the direct incorporation.

For imaging purposes, the imaging radionuclide is selected from $^{99m}Tc$; $^{87}Y$; $^{67}Ga$; $^{64}Cu$; and $^{111}In$. A preferred imaging radionuclide is $^{99m}Tc$. A compound of the invention comprising PACAP, or a biologically active PACAP fragment or analog, and an imaging radionuclide is an "imaging compound."

For therapeutic purposes, the "therapeutic radionuclide" is selected from $^{47}Sc$, $^{64}Cu$, $^{67}Ga$, $^{212}Pb$, 68Ga, $^{90}Y$, $^{111}In$, $^{153}Sm$, $^{212}Bi$, $^{210}At$, $^{211}At$, $^{177}Lu$, $^{186}Re$ and $^{188}Re$. Preferred therapeutic radionuclides are $^{90}Y$, $^{186}Re$ and $^{188}Re$. A compound of the invention comprising PACAP, or a biologically active PACAP fragment or analog, and a therapeutic radionuclide is a "therapeutic compound."

The imaging compounds of the invention can be used to detect VPAC-expressing tumors in a subject who has, or is suspected of having, such a tumor. As used herein, a "subject" is includes human and non-human mammals. Non-human mammals include bovines, ovines, porcines, equines, canines, felines, and rodents (e.g., rat, mouse, guinea pig and rabbit). Tumors which express VPAC receptors include tumors of the lung, breast, ovary, stomach, pancreas, larynx, esophagus, testes, liver, parotid, biliary tract, colon, rectum, cervix, uterus, endometrium, kidney, bladder, prostate and thyroid; squamous cell carcinomas; adenocarcinomas; small cell carcinomas; melanomas; and brain tumors such as gliomas and neuroblastomas.

In the practice of the invention, an effective amount of an imaging compound comprising PACAP, or a biologically active PACAP fragment or analog, is administered to a subject by any suitable enteral or parenteral route of administration. Parenteral administration is preferred.

Suitable parenteral administration methods include intravascular administration (e.g. intravenous bolus injection, intravenous infusion, intra-arterial bolus injection, intra-arterial infusion and catheter instillation into the vasculature); peri- and intra-tissue injection (e.g. peri-tumoral and intra-tumoral injection); subcutaneous injection or deposition including subcutaneous infusion (such as by osmotic pumps); and direct application to the tumor or to tissue surrounding the tumor, for example by a catheter or other placement device (e.g., a suppository or an implant comprising a porous, non-porous, or gelatinous material, a sialastic membrane, or a fiber). It is preferred that subcutaneous injections or infusions be given near the tumor or suspected tumor site, particularly if the tumor or suspected tumor site is on or near the skin. The imaging compound is preferably administered by intravascular injection in a single unit dose, for example in a conventional injection medium such as isotonic saline, blood plasma, or biologically compatible isotonic buffers (e.g., phosphate, Hepes or Tyrode's buffer).

When injected intravascularly, the present imaging compounds readily extravasate into solid tumors and distribute relatively evenly within the tumor mass, despite the presence of tight junctions between tumor cells, fibrous stroma, interstitial pressure gradients, and binding site barriers. Likewise, imaging compounds of the invention administered peri- or intra-tumorally will readily distribute within the tumor mass.

As used herein, an "effective amount" of an imaging compound of the invention is an amount sufficient to permit the generation of scintigriphic images of a PACAP- or VPAC-expressing tumor in the subject. The effective amount of imaging compound is conveniently expressed in terms of radioactivity; e.g., mCi. Generally, an effective amount of imaging compound is from about 0.01 mCi to about 100 mCi per 70 kg bodyweight, preferably from about 0.1 mCi to about 50 mCi per 70 kg bodyweight.

After the imaging compound is administered to the subject, a scintigriphic image is generated of at least part of the subject. For example, an image is desirably obtained of that part of the subject's body containing, or which is suspected of containing, the tumor. The scintigriphic image is generated after sufficient time has passed to allow the administered imaging compound to reach the tumor and bind to the PACAP and VPAC receptors on tumor cells. Typically, the imaging compound will reach and bind to the tumor within a few minutes of injection. However, imaging of the tumor can take place, if desired, several hours after injection of the imaging compound. The tumor can be imaged with any scintigriphic imaging technique, including planar scintigriphy, SPECT or PET. Techniques and machines for generating scintigriphic images of a subject are well-known in the art.

Radiolabeled pharmaceuticals are often retained in the kidneys. It is therefore desirable to minimize the renal retention of such agents, as this will minimize the radiation burden to the subject's organs and enhance tumor contrast. It is known that pre- or co-administration of an amino acid (e.g., lysine) with a radiolabeled pharmaceutical can significantly decrease renal uptake of the radiopharmaceutical. Therefore, the present imaging method optionally includes the pre- or co-administration of an amino acid to reduce renal uptake of the imaging compound. The amino acid can be administered by any suitable enteral or parenteral route as described above, which can be the same or different as the route of administration used for the imaging compound.

One or ordinary skill in the art can readily determine the amount of amino acid to be pre- or co-administered to the subject with the present imaging compounds, in order to inhibit renal uptake of the imaging compound. See, e.g., Kobayashi H et al., *Cancer Res.* 56: 3788–3795, 1996 Bernard B F et al., *J. Nucl. Med.* 38: 1929–1933, 1997; Behr T M et al., *Eur. J. Nucl Med.* 25: 201–212, 1998, the entire disclosures of which are herein incorporated by references.

Generally, the amount of amino acid to be pre- or co-administered with the present imaging compounds is from 0.1 to 5 g/kg bodyweight, preferably 0.4 to 2 g/kg bodyweight. A preferred amino acid to be pre- or co-administered is D-lysine.

It is understood that subjects who are only suspected of having a VPAC-expressing tumor, but who in fact do not have such a tumor, can undergo the imaging method of the invention. Of course, such subjects would produce a negative result.

The therapeutic compounds of the invention can be used to treat VPAC-expressing tumors in a subject who has such a tumor. In the practice of the invention, an effective amount of an therapeutic compound comprising PACAP, or a biologically active PACAP fragment or analog, is administered to a subject by any suitable enteral or parenteral route of administration, as described above for the imaging compounds. Intravascular or intra-tumoral administration is preferred. The present therapeutic compounds also readily extravasate into solid tumors and/or distribute relatively evenly within the tumor mass, as described above for the imaging compounds.

The effective amount of therapeutic compound is conveniently expressed in terms of radioactivity; e.g., mCi. As used herein, an "effective amount" of an therapeutic compound of the invention is an amount sufficient to inhibit or reverse the growth of VPAC-expressing tumor in the subject. The effective amount of the therapeutic compound administered to a given subject will depend on factors such as the mode of administration, the stage and severity of the tumor being treated, the weight and general state of health of the subject, and the judgment of the prescribing physician.

Generally, an effective amount of therapeutic compound administered to a subject is from about 1 mCi to about 1000 mCi per 70 kg bodyweight, preferably about 10 mCi to about 500 mCi per 70 kg bodyweight, more preferably about 20 mCi to about 100 mCi per 70 kg bodyweight. It is understood that the present therapeutic methods include multiple administrations of the therapeutic compound.

The present therapeutic method also optionally includes the pre- or co-administration of an amino acid to reduce renal uptake of the therapeutic compound, as discussed above. The doses and routes of administration of the amino acid are as described above for the imaging method. A preferred amino acid to be pre- or co-administered is D-lysine.

One of ordinary skill in the art can readily determine whether growth of a VPAC-expressing tumor is inhibited or reversed, for example by direct visual observation of tumor size before and after treatment using the imaging methods described above. Inhibition or reversal of tumor growth can also be determined by estimation tumor size before and after treatment by physical means, such as palpation of the tissue mass or measurement of the tissue mass with a measuring instrument such as a caliper.

The imaging and therapeutic compounds of the invention are preferably formulated as pharmaceutical compositions prior to administering to a subject, according to techniques known in the art. Pharmaceutical compositions of the present invention are characterized as being at least sterile and pyrogen-free. As used herein, "pharmaceutical formulations" include formulations for human and veterinary use.

The present pharmaceutical formulations comprise an imaging or therapeutic compound of the invention and a physiologically acceptable carrier medium. Preferred physiologically acceptable carrier media are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include physiologically biocompatible buffers (e.g., tromethamine hydrochloride), or additions (e.g., 1 to 50 mole percent) of calcium or sodium salts (for example, calcium chloride, calcium ascorbate, calcium gluconate or calcium lactate). The pharmaceutical composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc.

The present pharmaceutical composition can also comprise a therapeutic or imaging compound of the invention formulated as a neutral or salt form. Pharmaceutically acceptable salts of the imaging or therapeutic compounds include those formed with free amino groups such as those derived from hydrochloric, phosphoric, acetic, oxalic, and tartaric acids, and those formed with free carboxyl groups such as those derived from sodium, potassium, ammonium, calcium, ferric hydroxides, isopropylamine, triethylamine, 2-ethylamino ethanol, histidine, and procaine.

The invention will now be illustrated by the following non-limiting examples.

EXAMPLE 1

Preparation of TP 3475

An analog of $PACAP_{27}$, called TP 3475, was prepared according to the techniques set forth in U.S. Pat. No. 6,395,255, supra. TP 3475 consists of $PACAP_{27}$ linked to a Gly-(D)Ala-Gly-Gly chelating agent at the C-terminal end of $PACAP_{27}$. An Aba spacer is located between the chelating agent and $PACAP_{27}$.

Briefly, $PACAP_{27}$ was synthesized by standard solid phase synthesis techniques. The C-terminal Aba spacer and the Gly-(D)Ala-Gly-Gly chelating agent were linked to the $PACAP_{27}$ by sequential addition of the appropriate amino acid residues to the C-terminal end of $PACAP_{27}$, by continuing the solid phase synthesis reactions. The analog was designated as TP 3475 after its molecular weight (expected 3475.17, found 3475.18). The primary sequence of TP 3475 is shown in FIG. 2 and is given in SEQ ID NO: 5.

EXAMPLE 2

Radiolabeling TP 3475 with $^{99m}Tc$

TP 3475 was metallated with $^{99m}Tc$ according to the procedure of U.S. Pat. No. 6,395,255, supra. This metallization reaction, performed essentially as follows, produced an imaging compound of the invention called $^{99m}Tc$-TP 3475.

To a clean, nitrogen flushed, 10 ml siliconized glass vial were added 10 µg of TP 3475 in 10 µl acetate buffer pH 4.6 (100 µg $SnCl_2.2H_2O$ in 10 µl 0.005 M HCl and 300 µl of 0.067 M $Na_3PO_4$, pH 12). The contents of the vial were flash-frozen by placing the vial in acetone dry ice bath. The vial was then placed in a GeneVac lyophilizer and lyophilized for 2 hr, filled with nitrogen, and sealed and stored at −20° C. until the metallization reaction.

Figure 3:
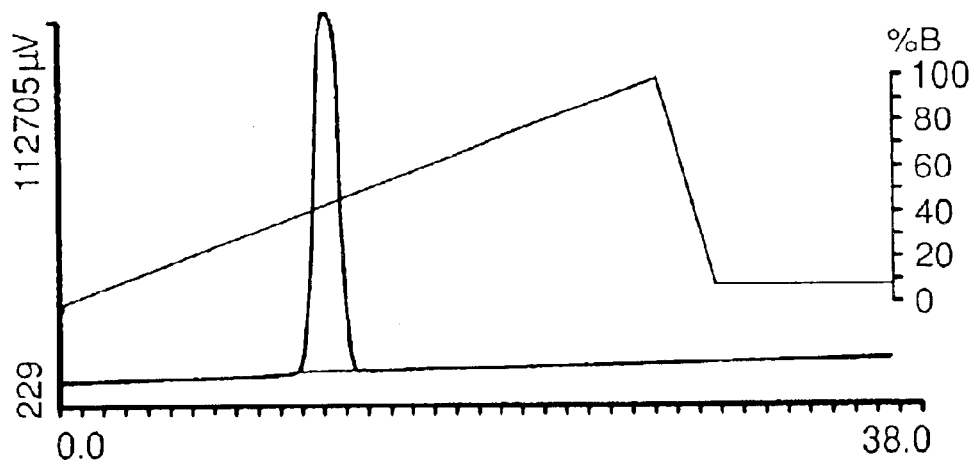
FIG. 3 is an HPLC elution profile of $^{99m}$Tc-TP 3475. 100% radioactivity is eluted in a single peak at retention time (Rt) 12.5 min. The Rt for TP 3475 (U.V.) is also 12.5 min. In this chromatogram, the U.V. peak is not detectable since quantity of TP 3475 injected was <0.01 μg. Free $^{99m}$Tc is eluted at Rt 3.2 min. The X axis is the elution time in min. The diagonal line represents gradient composition.
Figure 4:
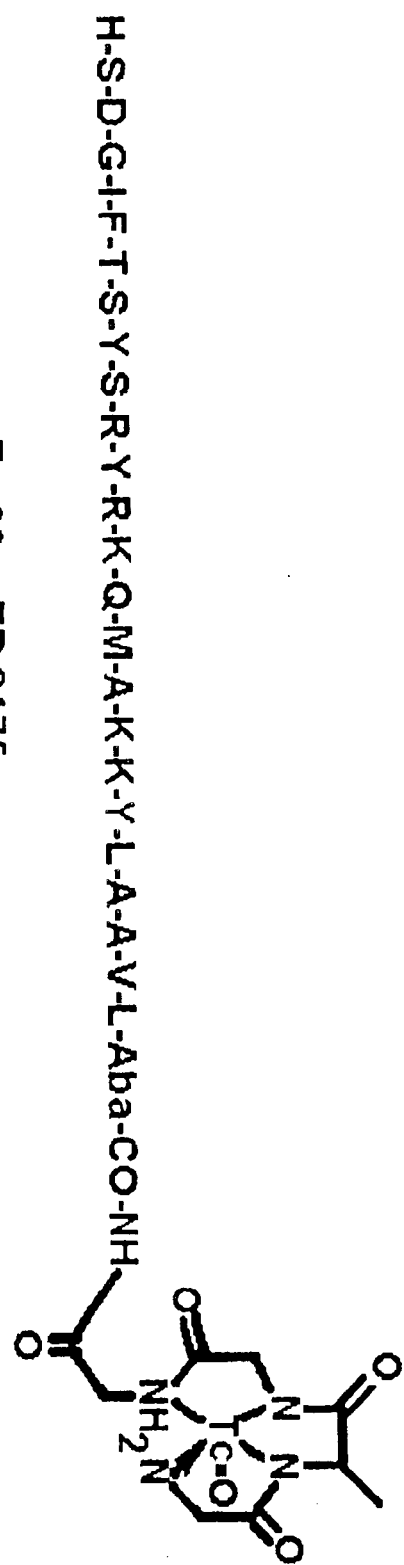
FIG. 4 is a schematic representing the structure of $^{99m}$Tc-TP 3475.

For the metallization reaction, the vial contents were allowed to come to ambient temperature, and 10–40 mCi $^{99m}Tc$ in 200 µl 0.9% NaCl was injected into the vial. The mixture was incubated at 100° C. for 30 min, and the pH of the reaction mixture was raised to 6–6.5 by addition of 1 ml 0.1 M $Na_2HPO_4$. One-hundred twenty-five mg of Na-ascorbate was added as a stabilizing agent. HPLC analysis of the metallated imaging compound $^{99m}Tc$-TP 3475 was performed on a Rainin HPLC with a reverse phase C-18 microbond column, using 0.1% TFA in $H_2O$ as solvent A and 0.1% TFA in acetonitrile as solvent B. The gradient was such that the solvent B was 10% at 0 min and 90% at 28 min. $^{99m}Tc$-TP 3475 was stable for 24 hr at 22° C. The yields at 22° C. are quantitative as determined by HPLC, producing a single peak at Rt. 12.5 min. The HPLC elution profile of $^{99m}Tc$-TP 3475 is given in FIG. 3, and the structure of $^{99m}Tc$-TP 3475 is shown in FIG. 4.

The stability of $^{99m}Tc$-TP 3475 was also evaluated for up to 24 hr at 37° C. in a 100 mM excess of cysteine, DTPA, and HSA. Similar studies were performed in human serum. HPLC analysis showed excellent stability of $^{99m}Tc$-TP 3475 in the media tested.

EXAMPLE 3

Evaluation of TP 3475 Binding to Breast Tumors

The binding of $^{99m}Tc$-TP 3475 and $VIP_{28}$ to human colon tumor cell lines LS 174T and HT-29, and the human breast cancer cell lines MDA MB 231 (estrogen-independent) and T47D (estrogen-dependent), is evaluated as follows. $^{125}I$-$PACAP_{27}$ is used as a control. Cells are grown in tissue culture and assays are performed as described in U.S. Pat. No. 6,395,255, supra. $IC_{50}$ and Kd values of TP 3475 $VIP_{28}$ and $^{125}I$-$PACAP_{27}$ are ascertained by standard methods.

Determination of cAMP activity as a function of dose—Approximately $5 \times 10^6$ cells from the estrogen-dependent T47D and estrogen-independent MDA MB 231 cell lines are washed twice with SIT medium and suspended in SIT medium containing 1% BSA, 1 mg/ml bacitracin, and 100 µM isobutyl-methyl-xanthine. TP 3475, $VIP_{28}$ and $^{125}I$-$PACAP_{27}$ are added to the cells in increasing concentrations, and five minutes later the reaction is quenched by addition of equal volume of ethanol. Samples are vortexed and frozen at −80° C. until assayed by cAMP RIA as described in Moody T W, *Peptides* 17: 545–555, 1995, the entire disclosure of which is herein incorporated by reference. Data are plotted as cAMP vs. peptide concentration.

Determination of c-fos and c-myc mRNA nuclear oncogene induction—The ability of TP 3475 to stimulate c-fos and c-myc gene expression in human breast tumor cells is evaluated. Approximately $5 \times 10^6$ cells from either the T47D and MDA MB 231 cell lines described above are cultured in 15 cm dishes and treated with SIT medium containing 0.5% fetal bovine serum for 4 hrs. TP 3475, $PACAP_{27}$ and $VIP_{28}$ are added separately to the cultured cells, and the cells are incubated for 60 min. After the incubation period, the medium is removed and total RNA is isolated from the treated cells using guanidinium isothiocynate method of Chirgwin et al., *Biochemistry* 18: 5294–5299,1979, the entire disclosure of which is herein incorporated by reference Ten µg of the total RNA isolated from the treated cells is denatured and separated in a 0.66 M formaldehyde-1% agarose gel. The gel is stained with ethidium bromide to assess RNA integrity. The RNA is then blotted onto a Nytran membrane overnight using standard techniques, and the membrane is hybridized with cDNA probes for c-fos and c-myc under standard Northern blot hybridization conditions. The c-fos and c-myc cDNA probes are labeled with [$^{32}P$]dCTP using a Bethesda Research Laboratories random priming kit according to the manufacturers instructions. The hybridized membrane is washed, and exposed to Kodak XAR-2 film and the autoradiogram is developed. Levels of c-fos and c-myc mRNA expression in the treated and control cells are quantified using a densitometer.

EXAMPLE 4

Effect of TP 3475 on Basal Tension of Opossum Internal Anal Sphincter (IAS) Smooth Muscle Tissue $PACAP_{27}$ is known to cause a concentration-dependent fall in the basal tension of IAS, by the assay described in Rattan S et al., *J. Pharmcol. Exper. Thera.* 263: 722–728, 1997, the entire disclosure of which is herein incorporated by reference. This IAS assay was performed with increasing concentrations of TP 3475 until a maximum fall is reached, essentially as described below. $PACAP_{27}$ was used as a control.

Preparation of smooth muscle strips—Adult opossums (*Didelphis virginiana*) of either sex were sacrificed after intra-peritoneal pentobarbital (40 mg/kg). The large blood vessels and extraneous tissues including the external and sphincter were removed, and the anal canal was opened and pinned flat with the mucosal side up on a dissecting tray containing oxygenated Krebs' solution (NaCl, 118.07; KCl, 4.69; $CaCl_2$, 2.52; $MgSO_4$, 1.16; $NaH_2PO_4$, 1.01; $NaHCO_3$, 25; and glucose, 11.10). The mucosa was removed, and internal anal sphincter circular smooth muscle strips (approximately 2 mm×1 cm) were prepared from the lowermost part of the anal canal.

Measurement of isometric tension—The IAS smooth muscle strips were transferred to temperature-controlled 2 ml "muscle baths" containing Krebs' solution, bubbled continuously with a mixture of 95% $O_2$-5% $CO_2$. With silk sutures, the lower end of the muscle strip was tied to the bottom of the muscle bath, whereas the other end was attached to an isometric force transducer (model FTO3; Grass Instruments Co, Quincy, Mass.). Isometric tensions were recorded on a Beckman Dynograph recorder (Beckman Instruments, Schiller Park, Ill.). Initially, 1 g of tension was applied to the muscle strips, and the strips were allowed to equilibrate for about 1 hr, with occasional washings. Only strips that developed steady tension and relaxed in response to electrical field stimulation were used. Both optimal length and base-line were determined as described in Rattan S et al., 1997, supra.

Figure 5:
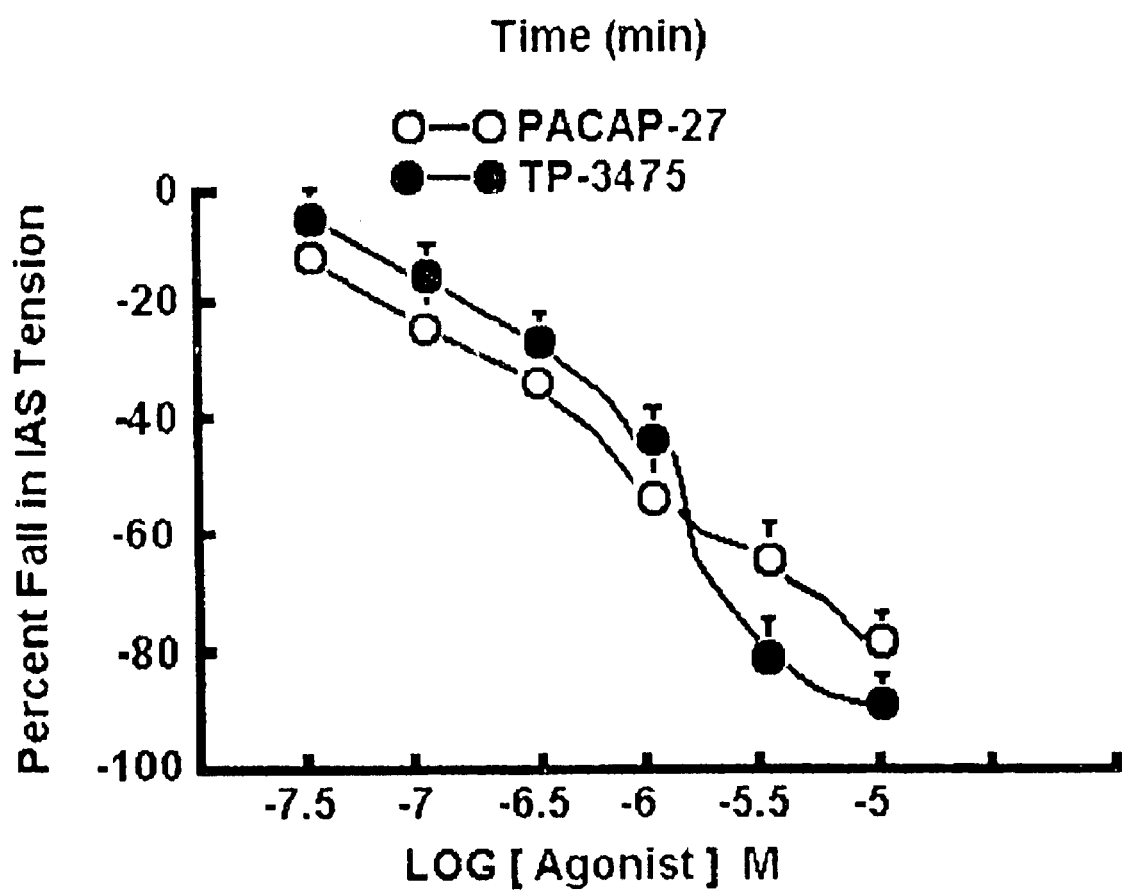
FIG. 5 is a plot showing the effect of increasing concentration of $PACAP_{27}$ and PACAP analog TP 3475 on resting opossum internal anal sphincter (IAS) smooth muscle tension. The data show that at $10^{-5}$ M concentration, the % fall in IAS tension was equal for both $PACAP_{27}$ and TP 3475.

The results shown in FIG. 5 demonstrate that at $10^{-5}$ M concentrations both $PACAP_{27}$ and TP 3475 caused an equivalent fall in IAS tension. These data indicate that the biological activity of TP 3475 was not compromised due to the addition of the spacer and chelating agent to the C-terminus of $PACAP_{27}$.

EXAMPLE 5

Tissue Distribution and Pharmacokinetics of $^{99m}$Tc-TP 3475 in Human Breast Tumor Cells Implanted in Nude Mice Studies are performed in nude mice bearing estrogen-dependent (T47D) or estrogen-independent (MDA MB 231) tumors as follows.

Approximately $5 \times 10^6$ viable cells from either tumor cell line are implanted in the right thigh of each mouse, and tumors are allowed to form. Each study group consists of 5 tumor-bearing mice which are injected through a lateral tail vein with a 200–700 μCi dose of $^{99m}$Tc-TP 3475, containing less than one microgram of the imaging compound (specific activity 1400–2500 Ci/mmol or higher). Animals are sacrificed at 15 min, 1 hr, 2 hr, 4 hr and 24 hr post-injection, and % of ID/g tissue is determined in all tissues. A control group of tumor-bearing mice is injected with $PACAP_{27}$ mono-iodinated with $^{125}$I. The $^{125}$I-$PACAP_{27}$ is adjusted to same specific activity as the $^{99m}$Tc-TP 3475 prior to injection into the control animals. All animals are imaged using a GE STARCAM gamma camera equipped with a dedicated computer and a low energy parallel hole collimator.

Results are presented numerically as well as in histograms arranged for a function of time. Tumor/muscle and tumor/blood ratios for the injected compounds are also calculated. In the animals sacrificed at 15 mins. post-injection, dynamic imaging studies are performed using a 15 sec frame. Using regions of interest, dynamic curves are plotted for tumor, heart, liver, kidneys, and bladder. These data, combined with other data points, allow for the determination of the uptake and clearance profile of radioactivity in each prominent organ, including tumors. To determine the chemical nature and the quantity of radioactivity excreted in the urine, animals are placed in metabolism cages. Radioactivity in the urine are measured periodically and urine samples are analyzed using HPLC.

EXAMPLE 6

Blood Clearance of $^{99m}$Tc-TP 3475 in the Rat

The blood clearance of $^{99m}$Tc-TP 3475 was studied in Sprague-Dawley rats as follows. Three Sprague Dawley rats, each weighing approximately 250 grams, were injected through one lateral tail vein with one mCi of $^{99m}$Tc-TP 3475, and serial blood samples were drawn in triplicate through the other lateral tail vein at 1, 5, 10, 15, and 30 minutes post-injection, and at 1, 2, 4, 6, 18 and 24 hours post injection. The blood samples were weighed, and radioactivity was counted against a standard $^{99m}$Tc solution prepared at the time of injection using standard scintillation counting techniques. The % ID/g plotted as a function of time.

The blood clearance of $^{99m}$Tc-TP 3475 was biphasic, with α-t½ being approximately 6 min and β-t½ being approximately 90 min. These data indicate that 75% of the radioactivity from injected $^{99m}$Tc-TP 3475 is cleared from the circulation in about 12 minutes.

EXAMPLE 7

Effect of Tumor Size and $^{99m}$Tc-TP 3475 Specific Activity on Tumor Uptake

Influence of Tumor Size on $^{99m}$Tc-TP 3475 Uptake—The influence of tumor size on imaging compound uptake is investigated in the tumor-bearing mice described in Example 5 above as follows. $^{99m}$Tc-TP 3475 and $^{125}$I-$PACAP_{27}$ (as a controls) are injected into the tumor-bearing mice. Tumor diameter is measured by vernier caliper. These studies are performed only at the optimal imaging time after injection, as determined by the tissue distribution studies of Example 5. Data are plotted as % ID/g vs. absolute tumor weight. In these experiments, specific activity of the compounds and the quantity of compound injected are kept constant, to maintain a uniform number of receptor-specific peptide molecules administered.

The Influence of Specific Activity of Injected $^{99m}$Tc-TP 3475 on Tumor Uptake—Tumor uptake of a receptor-specific imaging or therapeutic agent may vary as a function of injected mass of the receptor specific compound. The effect of the injected mass of $^{99m}$Tc-TP 3475, which is expressed in terms of specific activity, is studied in the tumor-bearing mice described in Example 5 above, as follows. Five $^{99m}$Tc-TP 3475 preparations are made which have a known specific activity in the range of 1000–25,000 Ci/mmol. Five separate groups of five tumor-bearing mice each are injected with a fixed quantity of radioactivity (~700 μCi) each containing 0.1, 0.5, 1, 1.5 or 2 μg of $^{99m}$Tc-TP 3475. Tissue distribution is evaluated at 24 hr post-injection. Uptake of the compounds in tumor and other tissue, and clearance of radioactivity from the tissues, is compared.

EXAMPLE 8

Minimization of Renal Uptake of $^{99m}$Tc-TP 3475

A treatment group of five mice are co-injected with 50 mg D-lysine and a 200–700 μCi dose of $^{99m}$Tc-TP 3475 containing less than one microgram of the imaging compound (specific activity 1400–2500 Ci/mmol or higher). A control group of five mice receive only the $^{99m}$Tc-TP 3475. Animals in the treatment and control groups are sacrificed at 15 min, 1 hr, 2 hr, 4 hr and 24 hr post-injection, and % ID/g in the kidney tissue is determined.

EXAMPLE 9

Receptor Specificity of $^{99m}$Tc-TP 3475

In order to determine receptor specificity of $^{99m}$Tc-TP3478 in human breast tumors, receptor blocking studies with PACAP were performed. In nude mice with T47D xenografts, $^{99m}$Tc-TP 3475 tumor uptake was reduced by approximately 50% when PACAP was pre-injected.

Another receptor blocking experiment is conducted as follows. Thirty minutes prior to intravenous injection of $^{99m}$Tc-TP 3475, tumor-bearing mice as described above are injected intravenously with up to 50 μg of TP 3475 in 100 μl of PBS. Animals are imaged at the optimal time determined from the tissue distribution studies of Example 5, and then sacrificed for quantitative tissue distribution studies. These data allow the determination of receptor specificity for $^{99m}$Tc-TP 3475, as indicated by the decreased radioactivity uptake in tumor tissue, and possibly in other organs such as the lungs, liver, and spleen.

EXAMPLE 10

Binding of $^{99m}$Tc-TP 3475 to Human Tumors

The binding of $^{99m}$Tc-TP 3475 and $^{99m}$Tc-VIP$_{28}$ to squamous cell carcinomas; adenocarcinomas; small cell carcinomas; melanomas; gliomas; neuroblastomas; and tumors of the lung, breast, ovary, stomach, pancreas, larynx, esophagus, testes, liver, parotid, biliary tract, colon, rectum, cervix, uterus, endometrium, kidney, bladder, brain, prostate and thyroid is evaluated as follows. $^{99m}$Tc-VIP$_{28}$ is prepared as described in U.S. Pat. No. 6,395,255, supra.

Samples of each tumor type are cut with a cryostat into 10–20 μm sections and mounted on microscope slides. The mounted slides are stored at −20° C. for at least three days, to improve adhesion of tissues to the slide. The slides are then warmed to reach ambient room temperature and incubated at 22° C. for 90 minutes in 50 mM Tris HCl, pH-7.4; 2% BSA; 2 mM EGTA; 1 mM bacitracin and 5 mm MgCl$_2$, with either 30 pM $^{99m}$Tc-TP 3475 or $^{99m}$Tc-VIP$_{28}$ in the presence or absence of monoiodinated $^{125}$I-PACAP$_{27}$ or $^{125}$I-VIP$_{28}$.

After incubation, the slides are washed 4× with ice-cold 50 mM Tris HCl, pH-7.4 and 0.25% BSA, 1× with water, and are dried under a stream of dry air. The slides are then exposed to $^3$H Ultra film (Amersham, England) for one week. Autoradiographs are quantified with a computer assisted image processing system. Films are also exposed with $^{125}$I autoradiographic standards. The Kd and the IC$_{50}$ value to inhibit specific binding of the radio-iodinated counterpart is determined for $^{99m}$Tc-TP 3475 or $^{99m}$Tc-VIP$_{28}$ in each tumor type.

EXAMPLE 11

Efficacy of $^{99m}$Tc-TP 3475 As Compared to $^{99m}$Tc-Sesta-MIBI and In-111-DTPA-D-Phe$^1$-Octreotide The efficacy of $^{99m}$Tc-TP 3475, $^{99m}$Tc-Sesta-MIBI and $^{111}$In-DTPA-D-Phe$^1$-Octreotide for imaging breast tumors was compared. $^{125}$I-PACAP was used as a control. $^{99m}$Tc-Sesta-MIBI, although not a receptor-specific agent, is approved by the FDA and is perhaps the most commonly used agent for breast imaging. $^{111}$In-DTPA-D-Phe$^1$-Octreotide is a commercially available imaging agent specific for one type of receptor (the SSTR receptor) on breast tumor cells.

$^{111}$In-DTPA-D-Phe$^1$-Octreotide and $^{99m}$Tc-Sesta-MIBI were obtained from the nuclear pharmacy. $^{99m}$Tc-TP 3475 was prepared as described above, and $^{125}$I-PACAP was prepared by standard techniques. The pharmacokinetics and tissue distribution of all agents in tumor-bearing mice were determined as in Example 5 above. Since SSTR and VPAC receptors are different, $^{99m}$Tc-TP 3475 and $^{111}$In-DTPA-D-Phe$^1$-Octreotide were co-injected into the tumor-bearing mice. The co-injected $^{99m}$Tc-TP 3475 and $^{111}$In-DTPA-D-Phe$^1$-Octreotide in the mouse tissues were counted by using the characteristic energy windows for their respective radionuclides (±15 or 20%); e.g., 140 KeV for $^{99m}$Tc, and 173 KeV and 247 KeV for $^{111}$In. The $^{111}$In counts in the tissues were again determined when $^{99m}$Tc was completely decayed (e.g., 10–12 half-lives).

The 24 hr tumor uptake of $^{99m}$Tc-TP 3475 was approximately 0.2% ID/g at 24 hr. This was about equal to the tumor uptake of $^{125}$I-PACAP (0.23±0.03% I.D./g), and was higher than the tumor uptake of $^{111}$In-DTPA-D-Phe$^1$-Octreotide (0.09±0.01% ID/g) and $^{99m}$Tc-Sesta-MIBI (0.18±0.0% I.D/g).

All documents referred to herein are incorporated by reference in their entirety. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

I claim:

1. A method of detecting tumors expressing VPAC receptors in a subject who has, or is suspected of having, such a tumor, said method comprising:
    (1) administering an effective amount of an imaging compound of formulae A or B to the subject; and
    (2) generating a scintigraphic image of at least part of the subject, wherein formulae A and B are:

M(I)-X$_1$-P-X$_2$ (A)

X$_1$-P-X$_2$-M(I) (B)

wherein:
    M is a chelating agent, provided that in formula A, when X$_1$ is zero and P is PACAP$_{27}$ (SEQ ID NO: 2), M is not a polyamino-polycarboxylic acid chelating agent;
    (I) is an imaging radionuclide conjugated to M;
    X$_1$ is from zero to twenty natural or synthetic amino acids;
    P is PACAP, or an analog or fragment thereof which exhibits PACAP biological activity; and
    X$_2$ is from zero to twenty natural or synthetic amino acids.

2. The method of claim 1, wherein M comprises an NxSy chelating compound.

3. The method of claim 2, wherein the NxSy chelating compound comprises an N2S2 or N3S core.

4. The method of claim 2, wherein the NxSy chelating compound comprises an N4 core.

5. The method of claim 2, wherein the NxSy chelating compound comprises MAG3 or Gly-(D)Ala-Gly-Gly.

6. The method of claim 1 wherein the chelating agent M of formula B comprises a polyamino-polycarboxylic acid.

7. The method of claim 1, wherein I is selected from the group consisting of $^{99m}$Tc; $^{87}$Y; $^{67}$Ga; $^{64}$Cu; and $^{111}$In.

8. The method of claim 7, wherein I is $^{99m}$Tc.

9. The method of claim 1, wherein the imaging compounds of formula A further comprise a spacer Z$_1$ linking X$_1$ and M, and the imaging compounds of formula B further comprise a spacer Z$_2$ linking X$_2$ and M.

10. The method of claim 9, wherein spacer Z$_1$ and spacer Z$_2$ separately comprise 4-amino butyric acid.

11. The method of claim 1, wherein P comprises SEQ ID NO: 2.

12. The method of claim 1, wherein the imaging compound is $^{99m}$TcTP 3475.

13. The method of claim 1 wherein the VPAC-expressing tumor is selected from the group consisting of lung; breast; ovary; stomach; pancreas; larynx; esophagus; testes; liver; parotid; biliary tract; colon; rectum; cervix; uterus; endometrium; kidney; bladder; brain; prostate; thyroid; squamous cell carcinoma; adenocarcinoma; small cell carcinoma; melanoma; gliomas; and neuroblastoma tumors.

14. The method of claim 1 wherein the subject is a non-human mammal.

15. The method of claim 1, wherein the effective amount of the imaging compound administered to the subject is from about 0.01 mCi to about 100 mCi per 70 kg bodyweight.

16. The method of claim 1, wherein the effective amount of the imaging compound administered to the subject is from about 0.1 mCi to about 50 mCi per 70 kg bodyweight.

17. The method of claim 1, further comprising the step of administering lysine either before or simultaneously with the imaging compound, such that renal uptake of the imaging compound is minimized.

18. A method of inhibiting or reversing the growth of a tumor expressing VPAC receptors in a subject who has such a tumor, comprising administering an effective amount of a composition of formulae C or D to the subject, wherein formulae C and D are

M(T)-X$_1$-P-X$_2$ (C)

X$_1$-P-X$_2$-M(T) (D)

and wherein:
    M is a chelating agent;
    (T) is a therapeutic radionuclide conjugated to M;
    X$_1$ is from zero to twenty natural or synthetic amino acids;
    P is PACAP or an analog or fragment thereof which exhibits PACAP biological activity; and
    X$_2$ is from zero to twenty natural or synthetic amino acids.

19. The method of claim 18, wherein M comprises an NxSy chelating compound.

20. The method of claim 19, wherein the NxSy chelating compound comprises an N2S2 or N3S core.

21. The method of claim 19, wherein the NxSy chelating compound comprises an N4 core.

22. The method of claim 21, wherein the NxSy chelating compound comprises MAG3 or Gly-(D)Ala-Gly-Gly.

23. The method of claim 18, wherein T is selected from the group consisting of $^{47}$Sc, $^{64}$Cu, $^{67}$Cu, $^{67}$Ga, $^{212}$Pb, $^{68}$Ga, $^{90}$Y, $^{111}$In, $^{153}$Sm, $^{212}$Bi, $^{210}$At, $^{211}$At, $^{177}$Lu, $^{186}$Re and $^{188}$Re.

24. The method of claim 23, wherein T is 90Y; $^{186}$Re; or 188Re.

25. The method of claim 18, wherein the therapeutic compounds of formula C further comprise a spacer $Z_1$ linking $X_1$ and M, and the therapeutic compounds of formula D further comprise a spacer $Z_2$ linking $X_2$ and M.

26. The method of claim 25, wherein spacer $Z_1$ and spacer $Z_2$ separately comprise 4-amino butyric acid.

27. The method of claim 18, wherein P comprises SEQ ID NO: 2.

28. The method of claim 18, wherein the VPAC-expressing tumor is selected from the group consisting of lung; breast; ovary; stomach; pancreas; larynx; esophagus; testes; liver; parotid; biliary tract; colon; rectum; cervix; uterus; endometrium; kidney; bladder; brain; prostate; thyroid; squamous cell carcinoma; adenocarcinoma; small cell carcinoma; melanoma; gliomas; and neuroblastoma tumors.

29. The method of claim 18, wherein the subject is a non-human mammal.

30. The method of claim 18, wherein the effective amount of the imaging compound administered to the subject is from about 1 mCi to about 1000 mCi per 70 kg bodyweight.

31. The method of claim 18, wherein the effective amount of the imaging compound administered to the subject is from about 10 mCi to about 500 mCi per 70 kg bodyweight.

32. The method of claim 18, wherein the effective amount of the imaging compound administered to the subject is from about 20 mCi to about 100 mCi per 70 kg bodyweight.

33. The method of claim 18, further comprising the step of administering lysine either before or simultaneously with the therapeutic compound, such that renal uptake of the therapeutic compound is minimized.

34. A compound of formulae A, B, C or D:

$$M(I)-X_1-P-X_2 \quad (A)$$

$$X_1-P-X_2-M(I) \quad (B)$$

$$M(T)-X_1-P-X_2 \quad (C)$$

$$X_1-P-X_2-M(T) \quad (D)$$

wherein:

M is a chelating agent; , provided that in formula A, when $X_1$ is zero and P is $PACAP_{27}$ (SEQ ID NO; 2), M is not a polyamino-polycarboxylic acid chelating agent;

(I) is an imaging radionuclide conjugated to M in formulae A and B;

(T) is a therapeutic radionuclide conjugated to M in formulae C and D;

$X_1$ is from zero to twenty natural or synthetic amino acids;

P is PACAP, or an analog or fragment thereof which exhibits PACAP biological activity; and $X_2$ is from zero to twenty natural or synthetic amino acids.

35. The compound according to claim 34, wherein M comprises an NxSy chelating compound.

36. The compound according to claim 35, wherein the NxSy chelating compound comprises an N2S2 or N3S core.

37. The compound according to claim 35, wherein the NxSy chelating compound comprises an N4 core.

38. The compound according to claim 35, wherein the NxSy chelating compound comprises MAG3 or Gly-(D) Ala-Gly-Gly.

39. The compound according to claim 34, wherein the chelating agent M comprises a polyamino-polycarboxylic acid.

40. The compound according to claim 34, wherein (I) is selected from the group consisting of $^{99m}Tc$; $^{87}Y$; $^{67}Ga$; $^{64}Cu$; and $^{111}In$.

41. The compound according to claim 34, wherein (T) is selected from the group consisting of $^{47}Sc$, $^{64}Cu$, $^{67}Cu$, $^{67}Ga$, $^{212}Pb$, $^{68}Ga$, $^{90}Y$, $^{111}In$, $^{153}Sm$, $^{212}Bi$, $^{210}At$, $^{211}At$, $^{177}Lu$, $^{186}Re$ and $^{188}Re$.

42. The compound according to claim 34, wherein the compounds of formulae A and C further comprise a spacer $Z_1$ linking $X_1$ and M, and the compounds of formulae B and D further comprise a spacer $Z_2$ linking $X_2$ and M.

43. The compound according to claim 42, wherein spacer $Z_1$ or spacer $Z_2$ comprises 4-amino butyric acid.

44. The compound according to claim 34, wherein P comprises SEQ ID NO:2.

45. The compound according to claim 34, wherein the compound is $^{99m}TCTP$ 3475.

* * * * *